United States Patent
Rudolph et al.

(10) Patent No.: US 9,511,021 B2
(45) Date of Patent: Dec. 6, 2016

(54) TABLETTABLE CHEWING GUMS

(75) Inventors: Markus Rudolph, Sulzbach (DE); Giovanna Marzano, Arzier (CH); Isabelle Rault, Segny (FR)

(73) Assignee: Novartis, A.G., Basel (CH)

( * ) Notice: Subject to any disclaimer, the term of this patent is extended or adjusted under 35 U.S.C. 154(b) by 516 days.

(21) Appl. No.: 12/993,188

(22) PCT Filed: May 19, 2009

(86) PCT No.: PCT/EP2009/056032
§ 371 (c)(1),
(2), (4) Date: Feb. 7, 2011

(87) PCT Pub. No.: WO2009/141321
PCT Pub. Date: Nov. 26, 2009

(65) Prior Publication Data
US 2011/0129517 A1    Jun. 2, 2011

(30) Foreign Application Priority Data
May 21, 2008 (EP) .................................. 08156636

(51) Int. Cl.
A61K 9/68     (2006.01)
A61K 31/465   (2006.01)

(52) U.S. Cl.
CPC ......... A61K 9/0058 (2013.01); A61K 31/465 (2013.01)

(58) Field of Classification Search
CPC ................................................. A61K 9/0058
USPC .......................................................... 424/48
See application file for complete search history.

(56) References Cited

U.S. PATENT DOCUMENTS

| | | | |
|---|---|---|---|
| 3,845,217 A | 10/1974 | Ferno | |
| 6,280,761 B1 | 8/2001 | Santus | |
| 6,344,222 B1 | 2/2002 | Cherukuri et al. | |
| 6,358,060 B2 | 3/2002 | Pinney | |
| 6,893,654 B2 | 5/2005 | Pinney | |
| 2002/0098264 A1 | 7/2002 | Cherukuri et al. | |
| 2002/0164398 A1 | 11/2002 | Johnson et al. | |
| 2004/0194793 A1 | 10/2004 | Lindell et al. | |
| 2005/0053665 A1* | 3/2005 | Ek et al. | 424/488 |
| 2005/0175733 A1* | 8/2005 | Thorengaard et al. | 426/3 |
| 2006/0263476 A1* | 11/2006 | Jani et al. | 426/3 |
| 2008/0020050 A1 | 1/2008 | Chau | |
| 2010/0061940 A1* | 3/2010 | Axelsson et al. | 424/48 |

FOREIGN PATENT DOCUMENTS

| | | |
|---|---|---|
| WO | WO01/89476 | 11/2001 |
| WO | WO02/102357 | 12/2002 |
| WO | WO2004/110492 | 12/2004 |
| WO | WO2005/023227 | 3/2005 |
| WO | WO2007/104574 | 9/2007 |
| WO | WO 2007104574 A2 * | 9/2007 |

OTHER PUBLICATIONS

SPI Pharma, Effer-Soda, 2007, www.spipharma.com/default.asp?contentID=592, pp. 1-2.*
EP2293786 opposition Fertin Pharma A/S against Novartis AG.
Exhibit D4 from EP2293786 opposition SPI Brochure.
Exhibit D6 from EP2293786 opposition Nicorette composition (BIAM fr).
Exhibit D8 from EP2293786 opposition Extract from "Formulation and Production of Chewing and Bubble Gum".

* cited by examiner

*Primary Examiner* — Benjamin Packard
(74) *Attorney, Agent, or Firm* — Joshua C. Sanders; Theodore R. Furman

(57) ABSTRACT

The invention relates to certain nicotine chewing gums that provide for a high rate of buccal absorption and high plasma concentrations, in particular over the first 10 minutes after administration, in a subject willing to quit smoking.

31 Claims, No Drawings

TABLETTABLE CHEWING GUMS

The present invention relates to certain chewing gums comprising nicotine. Dosage forms comprising nicotine have been widely used in the therapy of smoking cessation, with the goal of reducing tobacco craving by a nicotine replacement therapy.

Among the known oral dosage forms comprising nicotine, chewing gums have to be mentioned as the most popular ones. Commercial products, like Nicorette® , have been available since many years. Typically, it is intended therein that nicotine is absorbed through the buccal mucosa.

It is well accepted that quitters when using oral nicotine dosage forms, i.e. chewing gums but also e.g. lozenges, are generally under-dosed. The current in-use daily doses do not cover their real nicotine needs. This was shown with both chewing gums and lozenges, e.g. by self-titration experiments.

The present invention is based on the finding that nicotine chewing gums that are able to provide high plasma concentrations early on, especially over the first 10 minutes after administration,—this usually being also coupled with an early absorption peak ($t_{max}$)—do mimick the smoking of a cigarette best, do not present insurmountable toxicity issues and thus are often preferable in smoking cessation therapy, i.e. to reduce tobacco craving.

However, typical nicotine chewing gums known so far have turned out to be dosage forms which were releasing nicotine rather slowly and thus were not ideal to promote rapid transmucosal absorption. Furthermore, even when providing nicotine chewing gums with rapid release of nicotine, it was found that the rapid release of nicotine did not translate into fast buccal absorption of nicotine.

In the pharmacokinetic art, the rate of absorption is usually described by the use of the pharmacokinetic parameters "time to peak plasma concentration" ($t_{max}$) and "peak plasma concentration" ($C_{max}$). Other parameters which are even more indicative of the clinical onset of action are (1) the plasma concentrations reached 5 or 10 min after administration [C (5 min), C (10 min)] and, in particular, (2) the area under the pharmacokinetic curve (AUC) from t=0 (uptake of chewing gum) until various time points [e.g. AUC (0-5 min), AUC (0-10 min) or AUC (0-20 min)]. In the corresponding pharmacokinetic curves, the concentration of nicotine found in plasma (in ng/ml) is plotted against time (in h), see Test Example 4 (Table 3) below.

A successful attempt to provide a nicotine dosage form with an early absorption peak ($t_{max}$) is represented by nasal sprays comprising nicotine, which are commercially available. However, for many smokers it is not convenient to administer nicotine via the nasal mucosa several times a day. Moreover, irritation of the nose is an undesired side effect.

The latest trends in trying to obtain chewing gums with faster nicotine release can be seen from WO 2005/023227 A2 and WO2007/104574 A2.

In WO 2005/023227 A2, the focus is on "pharmaceutical formulations of nicotine wherein the nicotine is stabilized against degradation" and which have "a high content of stabile nicotine in a bioavailable form". Under "Prior art and problems thereof" it is said that the need for said pharmaceutical formulations "is not entirely achieved through nicotine formulations known in the art". As "traditional solid nicotine species" for use "in dosage forms such as gums and tablets" are mentioned "nicotine resin complex, nicotine β-cyclodextrin complex, and salts as e.g. nicotine bitartrate dihydrate". The solution offered by WO 2005/023227 A2 is to use as nicotine species "a cellulose carrier for administration of nicotine", in other words a "nicotine-cellulose matrix", more precisely a nicotine-cellulose matrix using "cellulose of non-seed organism origin" (e.g. obtained from algae).

In WO2007/104574 A2, it is strived for chewing gums which "provide rapid release of nicotine" and achieve "a fast onset of nicotine effect". The solution offered again is to use as nicotine species "a nicotine-cellulose combination", also named "nicotine-cellulose adduct" or "nicotine-cellulose carrier complex".

Both documents WO 2005/023227 A2 and WO2007/104574 A2 point to the presence of buffering agents in said oral nicotine formulations as an optional measure to raise the pH in the oral cavity and thus enhance the absorption of nicotine. They both also mention direct compression as a method for manufacturing nicotine chewing gums.

In clear contrast to WO 2005/023227 A2 and WO2007/104574 A2, it is an object of the present invention to provide a nicotine chewing gum which provides for a high rate of buccal (=oral mucosal) absorption of nicotine and for high plasma concentrations early on (especially over the first 10 minutes after administration)—usually coupled with an early plasma peak of nicotine (=short $t_{max}$)—but to achieve said goal with the use of "traditional solid nicotine species" and avoid the use of both sophisticated, new nicotine complexes, especially with celluloses, and liquid free nicotine base.

Therefore, the nicotine actives coming into consideration according to the present invention are pharmaceutically acceptable salts of nicotine and pharmaceutically acceptable nicotine complexes and resins, e.g. nicotine polacrilex, preferably pharmaceutically acceptable salts of nicotine.

Pharmaceutically acceptable nicotine salts are e.g. nicotine bitartrate, nicotine hydrochloride, nicotine dihydrochloride or nicotine sulfate, in particular nicotine bitartrate.

To summarize, an object of the present invention is to provide a nicotine chewing gum which provides for a high rate of buccal (=oral mucosal) absorption of nicotine and for an early plasma peak of nicotine (=short $t_{max}$), and which comprises traditional, solid, chemically stable nicotine actives, such as pharmaceutically acceptable salts of nicotine or nicotine resins, only.

A closely related but clinically even more relevant further object of the present invention is to provide a nicotine chewing gum, which provides high nicotine plasma concentrations over the first 10 minutes after administration, without unacceptable toxic effects, and which comprises traditional, solid, chemically stable nicotine actives, such as pharmaceutically acceptable salts of nicotine or nicotine resins, only.

The present invention provides a nicotine chewing gum with rapid nicotine release in the oral cavity. Said rapid nicotine release also translates into a fast—but non-toxic, pharmaceutically acceptable—buccal absorption of nicotine, as can be seen from shorter $t_{max}$ and higher $C_{max}$ values and, in particular, higher nicotine plasma concentrations over the first, e.g., 10 minutes after administration observed, which inter alia may be explained by the fact that a buffering agent is incorporated, preferably in homogeneous mixture.

Surprisingly, the presence of nicotine active and buffer, even in homogeneous mixture, does not lead to instability of the compositions but the chewing gums of the present invention are chemically and physically stable and have a shelf life of at least 12, preferably at least 24, months when stored at 25° C. and at a relative humidity of 60%. Without wishing to be bound by theory, this is believed mainly due to the followings reasons: (a) The manufacture of the chewing gums by tabletting and, (b), preferably, consistently at ambient temperature. In contrast to the usual manufacture of chewing gums by typically melting the mixture at 70-80° C., where a homogeneous mixture of all components on a molecular level is obtained, a less dispersed, preferably homogeneous, mixture is processed during tabletting at ambient temperature. This means that the contact between nicotine active and buffer, which is potentially jeopardizing stability, is less intimate here. (c) Preferably, the chewing gums of the present invention are coated, which means that access of water and oxygen—the two substances in general most jeopardizing stability—to the uncoated chewing gum core is hampered. Thus a particular embodiment of the invention is characterized by chewing gums as disclosed herein before and after, which are coated (in a way that access of water and oxygen to the uncoated chewing gum core is hampered). The composition of said coating is described herein further below.

Typically, $C_{max}$ values in the blood plasma of a patient of from 5 to 20 ng/ml, preferably of from 5 to 15 ng/ml, and more preferably of from 7 to 13 ng/ml, or 5 to 7 ng/ml, are reached. The increase of $C_{max}$ values might be limited by safety concerns regarding nicotine single doses. However, high $C_{max}$ values for nicotine chewing gums are generally desirable because any "too high" $C_{max}$ value may be mitigated by lowering the nicotine dose in the chewing gum. Thus, another object of the present invention is nicotine chewing gums, as disclosed in this document, with $C_{max}$ values of from 5 to 15 ng/ml, preferably of from 7 to 13 ng/ml and in particular of from 8 to 11 ng/ml, but with including a lower dose of nicotine active, e.g. an amount equivalent to 0.2 to 2 mg, especially 0.5 to 1 mg, of nicotine free base, only.

As already indicated above, a further object of the present invention is to provide nicotine chewing gums that can be manufactured by tabletting techniques, thus do not require the specific (e.g. melt extrusion) equipment necessary in the manufacture of conventional chewing gums.

The present invention thus relates to a chewing gum for use in nicotine replacement therapy, which provides rapid nicotine release in the oral cavity and fast—but non-toxic, pharmaceutically acceptable—buccal absorption of nicotine, and which is characterized by comprising a compressible chewing gum base that allows the chewing gum to be manufactured by tabletting, at least one nicotine active selected from the group consisting of pharmaceutically acceptable salts of nicotine and pharmaceutically acceptable nicotine complexes and resins, and at least one buffering agent.

Preferably, all the components of the chewing gum, including the compressible chewing gum base that allows the chewing gum to be manufactured by tabletting, the at least one nicotine active and the at least one buffering agent are in homogeneous mixture. To avoid any possible misunderstanding, the term "in homogeneous mixture" also e.g. includes the incorporation of a buffer agent like, for example, Effer-Soda™ 12 (SPI Pharma, UK)—see further explanations below—into the chewing gum mixture to be tabletted.

The term "tabletting" on the one hand includes, preferably, conventional tabletting techniques but also, on the other hand, any sophisticated ones. They all have in common the application of force, i.e. the compression of the mixture of all components of the chewing gum.

Chemically and physically stable means that the formulation has an acceptable pharmaceutical shelf life of at least 12, preferably at least 24, months when stored at 25° C. and at a relative humidity of 60% in a conventional pharmaceutical packaging. Thus in one embodiment of the invention, the chewing gums are chemically and physically stable and have a shelf life of at least 12, preferably at least 24, months when stored at 25° C. and at a relative humidity of 60%.

Rapid nicotine release means releasing nicotine in an in-vitro dissolution testing method (40 ml buffer pH 7.4, chewing jaw distance 1.6 mm-20° rotation, 50 chewing movements per minute) at least 60% in 5 minutes (250 chews), at least 70% in 10 minutes (500 chews) and more than 80% in 30 minutes (1500 chews) of the nicotine assay value. The apparatus to be used for these measurements is described in Kvist et al., Int J Pharm 189 (1999) 57-65. It is a device well known to be used for studying the in vitro drug release from medicated chewing gums.

Preferably, rapid nicotine release is characterized by an in vitro release of at least 60% in 5 minutes (250 chews), of at least 75% (more preferably at least 85%) in 10 minutes (500 chews) and more than 90% in 30 minutes (1500 chews) of the nicotine assay value.

Fast—but non-toxic, pharmaceutically acceptable—buccal absorption of nicotine typically is further characterized by high in-vivo truly delivered total doses of nicotine in the mouth of a patient over a time period of 30 minutes, e.g. by a delivery of at least 80%—preferably at least 90% and more preferably at least 95%—of the original amount of nicotine in the gum over 30 min.

Fast—but non-toxic, pharmaceutically acceptable—buccal absorption of nicotine typically is further characterized by reaching mean plasma concentrations C (5 min) of from 1 up to 6 ng/ml, preferably of from 1 up to 5 ng/ml and especially of from 1 up to 3 ng/ml.

Fast—but non-toxic, pharmaceutically acceptable—buccal absorption of nicotine typically is further characterized by reaching mean plasma concentrations C (10 min) of from 3 up to 14 ng/ml, preferably of from 3 up to 12 ng/ml and especially of from 3 up to 8 ng/ml.

Fast—but non-toxic, pharmaceutically acceptable—buccal absorption of nicotine typically is further characterized by reaching mean AUCs (0-10 min) of from 0.2 up to 0.9 ng×h/ml, preferably of from 0.2 up to 0.8 ng×h/ml and especially of from 0.2 up to 0.5 ng×h/ml.

Fast—but non-toxic, pharmaceutically acceptable—buccal absorption of nicotine typically is further characterized by reaching mean AUCs (0-20 min) of from 0.8 up to 3.2 ng×h/ml, preferably of from 0.8 up to 2.7 ng×h/ml and especially of from 0.8 up to 1.8 ng×h/ml.

Fast—but non-toxic, pharmaceutically acceptable—buccal absorption of nicotine means reaching a mean $t_{max}$ value in the blood plasma of a patient of 45 minutes or less, preferably of 35 minutes or less, more preferably of from 4 to 30 minutes, especially of from 10 to 30 minutes, more especially of from 15 to 30 minutes, and in particular of from 15 to 25 minutes; or of from 20 to 30 minutes, or of from 25 to 30 minutes. For example, for the 2 mg nicotine chewing gum of Example 14, mean $t_{max}$ values of 25 min (natural chew) and 30 min (forced chew) were measured.

Fast—but non-toxic, pharmaceutically acceptable—buccal absorption of nicotine typically is further characterized by reaching a mean $C_{max}$ value in the blood plasma of a patient of from 5 to 20 ng/ml, preferably of from 5 to 15 ng/ml, and more preferably of from 7 to 13 ng/ml, or of from 5 to 7 ng/ml. For example, for the 2 mg nicotine chewing gum of Example 14, mean $C_{max}$ values of 6.131 ng/ml (natural chew) and 6.525 ng/ml (forced chew) were measured, in direct comparison to a mean $C_{max}$ value of 4.779 ng/ml (chew & park) obtained for a Nicorette® 2 mg chewing gum under the same experimental conditions.

Typically, the nicotine chewing gums of the present invention comprise the nicotine active in an amount equivalent to 0.2 to 8 mg—preferably 0.5 to 8 mg, especially 1 to 4 mg and in particular 2 to 4 mg—of nicotine free base.

The buffering agent is e.g. an alkali metal carbonate, an alkali metal bicarbonate, an alkaline earth metal carbonate, an alkali metal citrate or an alkali metal phosphate, or any mixture thereof. Preferably, it is sodium carbonate, potassium carbonate, sodium bicarbonate, potassium bicarbonate, calcium carbonate, potassium citrate or dipotassium phosphate, or any mixture thereof. More preferably, the buffering agent is sodium carbonate, sodium bicarbonate, potassium carbonate, potassium bicarbonate, potassium citrate and dipotassium phosphate, or any mixture thereof. Especially, it is sodium carbonate, sodium bicarbonate, potassium carbonate or potassium bicarbonate, or any mixture thereof.

A special embodiment of the buffering agent is characterized by using two different buffering agents in the composition of the chewing gum, e.g. a mixture of an alkali metal bicarbonate with an alkali metal carbonate, such as a mixture of sodium bicarbonate and sodium carbonate.

Percentages given in this document are always intended to be weight-%, unless indicated otherwise.

An even more special embodiment of the buffering agent is characterized by using two different buffering agents, wherein one of the buffering agents is enrobing (coating) the other. As an example thereof, Effer-Soda™ 12 (SPI Pharma, UK) is mentioned, which constitutes a mixture of Na2CO3 and NaHCO3, wherein a core of NaHCO3 (ca. 85-95%) is coated by Na2CO3 (ca. 5-15%).

A compressible gum base that allows the chewing gum to be manufactured by tabletting typically is characterized by comprising from 20 to 40% of gum base and from 40-80%, preferably 50-80%, of at least one sugar alcohol.

"Gum base" means conventional gum bases that are widely used for the manufacture of conventional chewing gums typically by melt extrusion processes. It is well known in the art that said conventional gum bases are unsuitable for use in tabletting processes, i.e. for obtaining "tablets" by applying compression force.

Said gum bases typically comprise
a) elastomers, e.g. butyl rubber, natural rubber, polyisobutylene (PIB), polyvinylacetate (PVAc) or styrene-butadiene rubber (SBR),
b) plasticizers, e.g. methyl esters or glycerol esters of rosin, or polyterpenes,
c) texture agents, e.g. calcium carbonate or talc,
d) waxes, e.g. paraffin wax or microcrystalline wax,
e) lipids, e.g. pure or hydrogenated edible oils such as cottonseed, palm or soya oil, and
f) emulsifiers, e.g. lecithin or glycerol monostearate.

Moreover, they optionally may include further excipients, e.g. flavors, colorants or antioxidants.

A sugar alcohol is e.g. maltitol, sorbitol, mannitol, xylitol, erythritol, lactitol or isomalt.

Preferably, a compressible gum base is in powdered form.

Optionally, a compressible gum base comprises further excipients, e.g.
  plasticizers (e.g. from 0.1 to 5%), for example a mineral oil, a vegetable oil or a triglyceride;
  anticaking agents (e.g. from 0.1 to 3%), for example colloidal silicon dioxide (e.g. Aerosil®) or talcum;
  fillers, e.g. calcium carbonate,
  flavors, e.g. in liquid form, spray-dried or in encapsulated form,
  intense sweeteners, e.g. acesulfame K, sucralose, saccharin sodium or aspartame.

Several "ready to use"—powdered—compressible gum bases are commercially available, for example PHARMAGUM™ S and PHARMAGUM™ C (SPI Pharma), PG NEW NUTRA TA and MONDO T POWDERED GUM (Gum Base Co. S.p.A.), or All in gum SF and All in gum SF Cool (Cafosa Gum SA).

Apart from using one of the available "ready to use" compressible gum bases, it is of course also possible to incorporate the individual components of a compressible gum base, as outlined above, into the composition of the chewing gums of the present invention. Thus, the term "compressible chewing gum base that allows the chewing gum to be manufactured by tabletting" is also intended to cover any mixture comprising from 20 to 40% of gum base and from 40-80%, preferably 50-80%, of at least one sugar alcohol—as defined above in more detail.

The chewing gums according to the present invention, apart from their three main constituents—compressible chewing gum base, nicotine active and buffering agent—, optionally include further excipients. In particular, these can be, for example, lubricants (e.g. magnesium stearate), sugar alcohols (as defined above, especially mannitol), anti-caking agents (as defined above, especially colloidal silicon dioxide and/or talc, preferably both of them), intense sweeteners (as defined above, especially acesulfame K), flavors [as defined above, especially a mixture of peppermint flavor (powdered), levomenthol (solid) and—liquid—peppermint oil]. Further optional excipients that come into consideration are, for example, flow agents, e.g. colloidal silicon dioxide, antioxdants, e.g. BHT, abrasive agents for whitening the teeth, e.g. mineral salts such as calcium carbonate, or dyes, e.g. iron oxide or titanium oxide.

A special embodiment of the invention is characterized by those chewing gums, wherein the compressible chewing gum base that allows the chewing gum to be manufactured by tabletting in addition comprises 0.01-1%, preferably 0.04-0.2%, of peppermint oil. Apart from its known flavoring properties, peppermint oil, surprisingly, has turned out to be very beneficial to the texture of the chewing gums of the present invention by contributing to a very consumer-appealing mouthfeel of softness. As peppermint oil is a liquid, a special process of manufacture had to be developed to incorporate it successfully into a blend suitable for tabletting, which typically must be dry. Said special process comprises (A) reducing the particle size of the compressible gum base by milling, mixing with colloidal silicon dioxide, and, while continuing with mixing, spraying peppermint oil onto the mixture; and (B) only then adding all the rest of the components to the mixture.

Optionally, the chewing gums of the present invention, after manufacture by tabletting, can still be coated. The coating of chewing gums, generally, is known in the art. Although not indispensable, it is preferred to provide the chewing gums of the present invention with a coating, inter alia for the following reasons: By using a coating, the texture of the final chewing gum can be further improved, in particular the chewing gum can be provided with more crunchiness, especially by using maltitol in the coating mixture. Moreover, the presence of a coating can increase the stability of the chewing gum by hampering access of water and oxygen to the uncoated chewing gum core. Typically, sugar coatings or polymer coatings come into consideration, of which the sugar coatings are preferred. Thus, in one embodiment, the chewing gums of the invention are coated with a coating that comprises at least one sugar alcohol, preferably and surprisingly maltitol. Typically, the amount of coating is approximately 10-50%, preferably 20-35%, of the uncoated chewing gum. Typically, a sugar coating mixture comprises a sugar alcohol (e.g. maltitol, sorbitol, mannitol, xylitol, erythritol, lactitol or isomalt, in particular maltitol); a binder, be it, e.g., (a) a gum (e.g. arabic gum, tragacanth gum, guar gum, acacia gum, xanthan gum, alginic acid, salts of alginic acid e.g. sodium alginate, gellan gum, glucomannan gum, carrageenan gum, karaya gum, locust bean gum or tara gum, in particular arabic gum) or (b) a protein-type binder such as gelatin; and optionally flavors, dyes, and traces of any polishing agents used (especially talc and/or Carnauba wax).

If a coating is applied to the chewing gums of the present invention, it typically does not include any nicotine active.

A special embodiment of the invention is characterized by those chewing gums, which are coated with a coating that comprises maltitol (e.g. 80-95%, especially 85-93% of total coating mass) and peppermint oil (e.g. 0.5-3%, especially 0.5-2% of total coating mass). Said coating provides the chewing gums with an excellent texture combining a certain amount of softness but not too much softness (due to peppermint oil) with sufficient crunchiness (due to maltitol), as acknowledged by test persons.

In particular preferred is said presence of a coating comprising maltitol (e.g. 80-95%, especially 85-93% of total coating mass) and peppermint oil (e.g. 0.5-3%, especially 0.5-2% of total coating mass) in combination with the presence of peppermint oil in the compressible chewing gum base that allows the chewing gum to be manufactured by tabletting (e.g. 0.01-1%, preferably 0.04-0.2% of compressible chewing gum base), as outlined above.

In a very preferred embodiment of the invention, the chewing gums of the present invention are coated with a coating that comprises a sugar alcohol as defined above, in particular maltitol, and a gum as defined above, in particular arabic gum. Typically, the sugar alcohol is present in an amount of 80-95%, especially 85-93%, of the total coating mass. Typically, the gum is present in an amount of 1-10%, especially 3-8%, of the total coating mass.

In an even more preferred embodiment, the chewing gums of the present invention are coated with a coating that further comprises a coating-plastifying substance selected from the group consisting of glycerol, polyethylene glycol, propylene glycol, povidone (polyvinyl pyrrolidone), copovidone (=vinyl pyrrolidone vinyl acetate copolymer), hydroxypropyl cellulose, hydroxypropyl methylcellulose, hydroxypropyl methylcellulose phthalate, diethyl phthalate, dibutyl phthalate, diacetin, triacetin, triethyl citrate, dibutyl citrate, acetyl tributyl citrate, acetyl triethyl citrate and 2-pyrrolidone—typically in an amount of 0.5-10%, especially 0.5-5%, of the total coating mass. Preferred as coating-plastifying substance is glycerol.

Another embodiment of the invention is characterized by a chewing gum—for use in nicotine replacement therapy—which comprises a compressible chewing gum base that allows the chewing gum to be manufactured by tabletting, at least one nicotine active selected from the group consisting of pharmaceutically acceptable salts of nicotine and pharmaceutically acceptable nicotine complexes and resins, and at least one buffering agent; and wherein the at least one nicotine active and the at least one buffering agent are present in homogeneous mixture.

All definitions and specific embodiments that can be found hereinbefore as well as in dependent claims (starting with claim 3) are valid for said embodiment of the invention as outlined in the preceding paragraph as well.

The invention further relates to the use of a chewing gum, which comprises a compressible chewing gum base that allows the chewing gum to be manufactured by tabletting, at least one nicotine active selected from the group consisting of pharmaceutically acceptable salts of nicotine and pharmaceutically acceptable nicotine complexes and resins, and at least one buffering agent; and wherein the at least one nicotine active and the at least one buffering agent are present in homogeneous mixture; for providing rapid nicotine release in the oral cavity and fast—but non-toxic, pharmaceutically acceptable—buccal absorption of nicotine in nicotine replacement therapy; or—put another way—for providing relief from nicotine craving.

All definitions and specific embodiments that can be found hereinbefore as well as in dependent claims (starting with claim 3) are valid for said embodiment of the invention as outlined in the preceding paragraph as well.

The following examples are intended to illustrate the invention.

Example 1

Coated Nicotine Chewing Gum Comprising 6.40 mg Nicotine Bitartrate Dihydrate (Corresponding to 2 mg of Nicotine Free Base)

| Uncoated chewing gum (="tablet" core) | |
|---|---|
| Nicotine bitartrate dihydrate | 6.40 mg |
| "All in gum SF Cool" compressible gum base (Cafosa, Spain) | 1190.00 mg |
| Colloidal silicon dioxide (Aerosil ®) | 5.00 mg |
| Peppermint oil | 1.00 mg |
| Acesulfame K | 1.50 mg |
| Peppermint flavor, powdered | 50.00 mg |
| Levomenthol | 8.00 mg |
| Effer-Soda ™ 12 (SPI Pharma, UK) [=mixture of 6.00 mg Na2CO3 and 44.00 mg NaHCO3] | 50.00 mg |
| Mannitol SD-200 | 10.00 mg |
| Talc | 10.00 mg |
| Magnesium stearate | 15.00 mg |
| Total mass of uncoated chewing gum: | 1346.90 mg |
| Chewing gum coating | |
| Maltitol (provided as a 70% aqueous solution) | 460.00 mg |
| Arabic gum | 25.00 mg |
| Titanium dioxide | 5.00 mg |
| Peppermint oil | 6.50 mg |
| Levomenthol | 4.30 mg |
| Coated chewing gum mass: | 1847.70 mg |

Process of Manufacturing Uncoated Chewing Gums ("Tablet Cores")

Process alternative 1: Introduce into a high shear mixer the compressible gum base milled through a hammer mill fitted with a 40 inches grate (=1.02 mm mesh) and the colloidal silicon dioxide. Mix the mixture. The peppermint oil is sprayed onto the mixture while the chopper and mixer are operating. The nicotine active, acesulfame, levomenthol, flavor, sodium carbonate, sodium bicarbonate, mannitol and talc are added. The mixture is mixed again. Magnesium stearate is added and the mixture is mixed again. Compress the mixture into chewing gums ("tablets") using a conventional rotary tabletting machine.

Process alternative 2: Introduce into a container the compressible gum base milled through a hammer mill fitted with a 40 inches grate (=1.02 mm mesh) and the silicon dioxide. The mixture is blended using a freefall blender. The nicotine active, acesulfame, levomenthol, flavor, sodium carbonate, sodium bicarbonate, mannitol and talc are added. The mixture is mixed again. Screen the mixture through a 1.0 mm grate. Magnesium stearate is added and the mixture is mixed again. Compress the mixture into chewing gums ("tablets") using a conventional rotary tabletting machine.

Process alternative 1 is preferably used for Examples 1-11, 21-23 and 26, i.e. for compositions including a liquid, namely peppermint oil.

Process alternative 2 is preferably used for Examples 12-20, 24-25 and 27-28.

Process of coating uncoated chewing gums: Dissolve maltitol in water while stirring and heating at 70-80° C. Add the gum arabic and titanium dioxide. Maintain the syrup formed at 70° C. during the process. The syrup suspension is applied on the rotating uncoated chewing gums ("tablet cores") and dispersed on their surface. Water is evaporated with warm inlet air (20-40° C.). The process is repeated until the total coating weight is reached (approximately 20-35% of the uncoated chewing gum mass).The flavor is added during the coating process. At the end of the process the coated chewing gums are polished with talc and Carnauba wax. Approximately 240-300 minutes time are required to apply 30% coating layer on the uncoated chewing gums.

Example 2-4

Coated Nicotine Chewing Gums Comprising the Equivalent of 2 mg of Nicotine Base

|  | Example 2 | Example 3 | Example 4 |
|---|---|---|---|
| Composition of uncoated chewing gum |  |  |  |
| (Equivalent of Nicotine base included) | (2.0) | (2.0) | (2.0) |
| Compressible gum base (All in Gum SF Cool, Cafosa) | 890.0 | 890.0 | 1190.0 |
| Aerosil ® | 5.0 | 5.0 | 5.0 |
| Acesulfame K | 1.5 | 1.5 | 1.5 |
| Mint flavor | 30.0 | 30.0 | 50.0 |
| Peppermint oil | 2.0 | 1.0 | 1.0 |
| Levomenthol | 8.0 | 8.0 | 8.0 |
| Coated sodium bicarbonate (Effersoda 12) | 50.0 | 50.0 | 50.0 |
| Sodium Carbonate | — | — | — |
| Sodium Bicarbonate | — | — | — |
| Mannitol | 10.0 | 10.0 | 10.0 |
| Talc | 10.0 | 10.0 | 10.0 |
| Nicotine bitartrate dihydrate | 6.2 | — | 6.4 |
| Nicotine Polacrilex 15% | — | 13.0 | — |
| Nicotine Polacrilex 20% | — | — | — |
| Nicotine Polacrilex 25% | — | — | — |
| Magnesium stearate | 15.0 | 15.0 | 15.0 |
| Uncoated chewing gum mass | 1022.7 | 1053.5 | 1346.9 |
| Composition of the chewing gum coating |  |  |  |
| Maltitol (provided as a 70% aqueous solution) | 424.8 | 424.8 | 491.5 |
| Arabic gum | 35.0 | 35.0 | 35.0 |
| Titanium dioxide | 7.0 | 7.0 | 7.0 |
| Peppermint oil | 6.7 | 6.7 | 6.7 |
| Levomenthol | 2.9 | 2.9 | 2.9 |
| Talc | q.s. (<0.1) | q.s. (<0.1) | q.s. (<0.1) |
| Carnauba wax | q.s. (<0.1) | q.s. (<0.1) | q.s. (<0.1) |
| Coated chewing gum mass | 1499.1 | 1529.9 | 1890.0 |

Examples 5-7

Coated and Uncoated Nicotine Chewing Gums Comprising the Equivalent of 2 mg of Nicotine Base

| Composition of uncoated chewing gum | Example 5 | Example 6 | Example 7 |
|---|---|---|---|
| (Equivalent of Nicotine base included) | (2.0) | (2.0) | (2.0) |
| Compressible gum base (All in Gum SF Cool, Cafosa) | 1490.0 | 1490.0 | 1190.0 |
| Aerosil ® | 5.0 | 5.0 | 5.0 |
| Acesulfame K | 1.5 | 1.5 | 1.5 |
| Mint flavor | 50.0 | 50.0 | 50.0 |
| Peppermint oil | 1.0 | 1.0 | 1.0 |
| Levomenthol | 8.0 | 8.0 | 8.0 |
| Coated sodium bicarbonate (Effersoda 12) | — | — | — |
| Sodium Carbonate | 10.0 | 10.0 | 10.0 |
| Sodium Bicarbonate | 20.0 | 20.0 | 20.0 |
| Mannitol | 10.0 | 10.0 | 10.0 |
| Talc | 10.0 | 10.0 | 10.0 |
| Nicotine bitartrate dihydrate | 6.4 | — | — |
| Nicotine Polacrilex 15% | — | 13.4 | — |
| Nicotine Polacrilex 20% | — | — | — |
| Nicotine Polacrilex 25% | — | — | 8.2 |
| Magnesium stearate | 15.0 | 15.0 | 15.0 |
| Uncoated chewing gum mass | 1626.9 | 1633.9 | 1328.7 |

| Composition of the chewing gum coating | Example 5 | Example 6 (uncoated) | Example 7 (uncoated) |
|---|---|---|---|
| Maltitol (provided as a 70% aqueous solution) | 673.5 |  |  |
| Arabic gum | 35.0 |  |  |
| Titanium dioxide | 7.0 |  |  |
| Peppermint oil | 6.7 |  |  |
| Levomenthol | 2.9 |  |  |
| Talc | q.s. (<0.1) |  |  |
| Carnauba wax | q.s. (<0.1) |  |  |
| Coated chewing gum mass | 2352.0 |  |  |

Examples 8-10

Uncoated and Coated Nicotine Chewing Gums Comprising the Equivalent of 2 or 1 mg of Nicotine Base, Respectively

|  | Example 8 | Ex. 9 | Example 10 |
|---|---|---|---|
| Composition of uncoated chewing gum |  |  |  |
| (Equivalent of Nicotine base included) | (2.0) | (1.0) | (2.0) |
| Compressible gum base (All in Gum SF Cool, Cafosa) | 1190.0 | 1190.0 | 1190.0 |
| Aerosil ® | 5.0 | 5.0 | 5.0 |
| Acesulfame K | 1.5 | 1.5 | 1.5 |
| Mint flavor | 50.0 | 50.0 | 50.0 |
| Peppermint oil | 1.0 | 1.0 | 1.0 |
| Levomenthol | 8.0 | 8.0 | 8.0 |
| Coated sodium bicarbonate (Effersoda 12) | — | 50.0 | 50.0 |
| Sodium Carbonate | 10.0 | — | — |
| Sodium Bicarbonate | 20.0 | — | — |
| Mannitol | 10.0 | 10.0 | 10.0 |
| Talc | 10.0 | 10.0 | 10.0 |

-continued

|  | Ex. 9 | Example 10 |
| --- | --- | --- |
| Nicotine bitartrate dihydrate | — | 3.2 | — |
| Nicotine Polacrilex 15% | — | — | — |
| Nicotine Polacrilex 20% | 9.9 | — | 9.5 |
| Nicotine Polacrilex 25% | — | — | — |
| Magnesium stearate | 15.0 | 15.0 | 15.0 |
| Uncoated chewing gum mass | 1330.4 | 1343.7 | 1350.0 |
|  | Example 8 (uncoated) | | |
| Composition of the chewing gum coating | | | |
| Maltitol (provided as a 70% aqueous solution) |  | 394.8 | 394.8 |
| Arabic gum |  | 21.0 | 21.0 |
| Titanium dioxide |  | 4.2 | 4.2 |
| Peppermint oil |  | 6.5 | 6.5 |
| Levomenthol |  | 4.3 | 4.3 |
| Talc |  | qs (<0.1) | q.s. (<0.1) |
| Carnauba wax |  | qs (<0.1) | q.s. (<0.1) |
| Coated chewing gum mass |  | 1774.5 | 1780.8 |

Examples 11-13

Coated and Uncoated Nicotine Chewing Gums Comprising the Equivalent of 2 or 4 mg of Nicotine Base, Respectively

|  | Example 11 | Ex. 12 | Example 13 |
| --- | --- | --- | --- |
| Composition of uncoated chewing gum | | | |
| (Equivalent of Nicotine base included) | (2.0) | (2.0) | (4.0) |
| Compressible gum base (All in Gum SF Cool, Cafosa) | 1190.0 | 1190.0 | 890.0 |
| Aerosil ® | 5.0 | 5.0 | 5.0 |
| Acesulfame K | 1.5 | 1.5 | 1.5 |
| Mint flavor | 50.0 | 50.0 | 30.0 |
| Peppermint oil | 1.0 | — | — |
| Levomenthol | 8.0 | 10.0 | 10.0 |
| Coated sodium bicarbonate (Effersoda 12) | 50.0 | 50.0 | 30.0 |
| Sodium Carbonate | — | — | — |
| Sodium Bicarbonate | — | — | — |
| Mannitol | 10.0 | 10.0 | 10.0 |
| Talc | 10.0 | 10.0 | 10.0 |
| Nicotine bitartrate dihydrate | 6.4 | 6.4 | 12.2 |
| Nicotine Polacrilex 15% | — | — | — |
| Nicotine Polacrilex 20% | — | — | — |
| Nicotine Polacrilex 25% | — | — | — |
| Magnesium stearate | 15.0 | 15.0 | 15.0 |
| Uncoated chewing gum mass | 1346.9 | 1347.9 | 1013.7 |
|  |  |  | Example 13 (uncoated) |
| Composition of the chewing gum coating | | | |
| Maltitol (provided as 70% aqueous solution) | 460.6 | 460.6 |  |
| Arabic gum | 24.5 | 24.5 |  |
| Titanium dioxide | 4.9 | 4.9 |  |
| Peppermint oil | 6.5 | 7.5 |  |
| Levomenthol | 4.3 | 4.3 |  |
| Talc | q.s. (<0.1) | q.s. (<0.1) |  |
| Carnauba wax | q.s. (<0.1) | q.s. (<0.1) |  |
| Coated chewing gum mass | 1847.7 | 1849.7 |  |

Examples 14-16

Coated Nicotine Chewing Gums Comprising the Equivalent of 2 mg of Nicotine Base Each

|  | Example 14 | Ex. 15 | Example 16 |
| --- | --- | --- | --- |
| Composition of uncoated chewing gum | | | |
| (Equivalent of Nicotine base included) | (2.0) | (2.0) | (2.0) |
| Compressible gum base (All in Gum SF Cool, Cafosa) | 1190.0 | 1190.0 | 1190.0 |
| Aerosil ® | 5.0 | 5.0 | 5.0 |
| Acesulfame K | 1.5 | 1.5 | 1.5 |
| Mint flavor | 50.0 | 50.0 | 50.0 |
| Taste masking flavor | — | 14.0 | 14.0 |
| Levomenthol | 8.0 | 8.0 | 8.0 |
| Coated sodium bicarbonate (Effersoda 12) | 50.0 | 50.0 | 50.0 |
| Mannitol | 10.5 | 10.5 | 10.5 |
| Talc | 10.0 | 10.0 | 10.0 |
| Nicotine bitartrate dihydrate | 6.14 | 6.14 | 6.14 |
| Magnesium stearate | 15.0 | 15.0 | 15.0 |
| Uncoated chewing gum mass | 1346.14 | 1360.14 | 1360.14 |
| Composition of the chewing gum coating | | | |
| Maltitol (provided as 70% aqueous solution) | 461.0 | 451.2 | 456.1 |
| Maltitol powder | 66.7 | 66.7 | 66.7 |
| Arabic gum | 24.5 | 24.5 | 24.5 |
| Glycerol | — | 9.8 | — |
| Povidone K-30 | — | — | 4.9 |
| Titanium dioxide | 4.9 | 4.9 | 4.9 |
| Peppermint oil | 7.5 | 7.5 | — |
| Fruit flavor | — | — | 25.0 |
| Levomenthol | 4.3 | 4.3 | 4.3 |
| Talc | q.s. (<0.1) | q.s. (<0.1) | q.s. (<0.1) |
| Carnauba wax | q.s. (<0.1) | q.s. (<0.1) | q.s. (<0.1) |
| Coated chewing gum mass | 1915.0 | 1929.0 | 1946.5 |

Examples 17-19

Coated and Uncoated Nicotine Chewing Gums Comprising the Equivalent of 2 mg of Nicotine Base Each

|  | Example 17 | Ex. 18 | Example 19 |
| --- | --- | --- | --- |
| Composition of uncoated chewing gum | | | |
| (Equivalent of Nicotine base included) | (2.0) | (2.0) | (2.0) |
| Compressible gum base (All in Gum SF Cool, Cafosa) | 1190.0 | 1190.0 | 1190.0 |
| Aerosil ® | 5.0 | 5.0 | 5.0 |
| Acesulfame K | 1.5 | 1.5 | 1.5 |
| Mint flavor | 50.0 | 50.0 | 50.0 |
| Taste masking flavor | 14.0 | 14.0 | 14.0 |
| Levomenthol | 8.0 | 8.0 | 8.0 |
| Coated sodium bicarbonate (Effersoda 12) | 50.0 | 50.0 | 50.0 |
| Mannitol | 10.5 | 10.5 | 10.5 |
| Talc | 10.0 | 10.0 | 10.0 |
| Nicotine bitartrate dihydrate | 6.14 | 6.14 | 6.14 |

-continued

| | Example 17 | Ex. 18 | Example 19 |
|---|---|---|---|
| Magnesium stearate | 15.0 | 15.0 | 15.0 |
| Uncoated chewing gum mass | 1360.14 | 1360.14 | 1360.14 |
| Composition of the chewing gum coating | | | |
| Maltitol (provided as 70% aqueous solution) | 446.3 | 446.3 | 451.2 |
| Maltitol powder | 66.7 | 66.7 | 66.7 |
| Arabic gum | 24.5 | 24.5 | 34.3 |
| Povidone K-30 | 14.7 | — | — |
| Copovidone VA 64 | — | 14.7 | — |
| Titanium dioxide | 4.9 | 4.9 | 4.9 |
| Peppermint oil | 7.5 | 7.5 | 7.5 |
| Levomenthol | 4.3 | 4.3 | 4.3 |
| Talc | q.s. (<0.1) | q.s. (<0.1) | q.s. (<0.1) |
| Carnauba wax | q.s. (<0.1) | q.s. (<0.1) | q.s. (<0.1) |
| Coated chewing gum mass | 1929.0 | 1929.0 | 1929.0 |

Examples 20-22

Uncoated Nicotine Chewing Gums Comprising the Equivalent of 4 mg of Nicotine Base Each

| Composition of uncoated chewing gum | Example 20 | Ex. 21 | Example 22 |
|---|---|---|---|
| (Equivalent of Nicotine base included) | (4.0) | (4.0) | (4.0) |
| Compressible gum base (All in Gum SF Cool, Cafosa) | 890.0 | 890.0 | 890.0 |
| Aerosil ® | 5.0 | 5.0 | 5.0 |
| Acesulfame K | 1.5 | 1.5 | 1.5 |
| Mint flavor | 30.0 | 30.0 | 30.0 |
| Peppermint oil | | | |
| Levomenthol | 10.0 | 10.0 | 10.0 |
| Coated sodium bicarbonate (Effersoda 12) | 50.0 | | |
| Sodium Carbonate | | 20.0 | 10.0 |
| Sodium Bicarbonate | | | 20.0 |
| Mannitol | 10.0 | 10.0 | 10.0 |
| Talc | 10.0 | 10.0 | 10.0 |
| Nicotine bitartrate dihydrate | 12.2 | 12.2 | 12.2 |
| Nicotine Polacrilex 15% | | | |
| Nicotine Polacrilex 20% | | | |
| Nicotine Polacrilex 25% | | | |
| Magnesium stearate | 15.0 | 15.0 | 15.0 |
| Uncoated chewing gum mass | 1033.7 | 1003.7 | 1013.7 |

Examples 23-25

Uncoated Nicotine Chewing Gums Comprising the Equivalent of 4 mg of Nicotine Base Each

| Composition of uncoated chewing gum | Example 23 | Ex. 24 | Example 25 |
|---|---|---|---|
| (Equivalent of Nicotine base included) | (4.0) | (4.0) | (4.0) |
| Compressible gum base (All in Gum SF Cool, Cafosa) | 890.0 | 890.0 | 890.0 |
| Aerosil ® | 5.0 | 5.0 | 5.0 |
| Acesulfame K | 1.5 | 1.5 | 1.5 |
| Mint flavor | 30.0 | 30.0 | 30.0 |
| Peppermint oil | | | |
| Levomenthol | 10.0 | 10.0 | 10.0 |
| Coated sodium bicarbonate (Effersoda 12) | 30.0 | 50.0 | |
| Sodium Carbonate | | | 20.0 |
| Sodium Bicarbonate | | | |
| Mannitol | 10.0 | 10.0 | 10.0 |
| Talc | 10.0 | 10.0 | 10.0 |
| Nicotine bitartrate dihydrate | | | |
| Nicotine Polacrilex 15% | 15.3 | 15.3 | 15.3 |
| Nicotine Polacrilex 20% | | | |
| Nicotine Polacrilex 25% | | | |
| Magnesium stearate | 15.0 | 15.0 | 15.0 |
| Uncoated chewing gum mass | 1016.8 | 1036.8 | 1006.8 |

Examples 26-28

Uncoated Nicotine Chewing Gums Comprising the Equivalent of 4 mg of Nicotine Base Each

| Composition of uncoated chewing gum | Example 26 | Ex. 27 | Example 28 |
|---|---|---|---|
| (Equivalent of Nicotine base included) | (4.0) | (4.0) | (4.0) |
| Compressible gum base (All in Gum SF Cool, Cafosa) | 890.0 | 890.0 | 890.0 |
| Aerosil ® | 5.0 | 5.0 | 5.0 |
| Acesulfame K | 1.5 | 1.5 | 1.5 |
| Mint flavor | 30.0 | 30.0 | 30.0 |
| Peppermint oil | | 1.0 | 2.0 |
| Levomenthol | 10.0 | 10.0 | 10.0 |
| Coated sodium bicarbonate (Effersoda 12) | | 50.0 | 50.0 |
| Sodium Carbonate | 10.0 | | |
| Sodium Bicarbonate | 20.0 | | |
| Mannitol | 10.0 | 10.0 | 10.0 |
| Talc | 10.0 | 10.0 | 10.0 |
| Nicotine bitartrate dihydrate | | 12.2 | 12.2 |
| Nicotine Polacrilex 15% | 15.3 | | |
| Nicotine Polacrilex 20% | | | |
| Nicotine Polacrilex 25% | | | |
| Magnesium stearate | 15.0 | 15.0 | 15.0 |
| Uncoated chewing gum mass | 1016.8 | 1034.7 | 1035.7 |

Examples 29-31

Uncoated and Coated Nicotine Chewing Gums Comprising the Equivalent of 4 or 2 mg of Nicotine Base

| Composition of uncoated chewing gum | Example 29 | Ex. 30 | Example 31 |
|---|---|---|---|
| (Equivalent of Nicotine base included) | (4.0) | (2.0) | (2.0) |
| Compressible gum base (All in Gum SF Cool, Cafosa) | 890.0 | 1190.0 | 1190.0 |
| Aerosil ® | 5.0 | 5.0 | 5.0 |
| Acesulfame K | 1.5 | 1.5 | 1.5 |
| Mint flavor | 30.0 | 50.0 | 50.0 |
| Peppermint oil | 7.0 | — | — |
| Levomenthol | 10.0 | 10.0 | 10.0 |

|  | Ex. 30 | Example 31 |
| --- | --- | --- |
| Coated sodium bicarbonate (Effersoda 12) | 50.0 | 50.0 | 50.0 |
| Sodium Carbonate | — | — |
| Sodium Bicarbonate | — | — |
| Mannitol | 10.0 | 10.0 | 10.0 |
| Talc | 10.0 | 10.0 | 10.0 |
| Nicotine bitartrate dihydrate | 12.2 | 6.4 | 6.4 |
| Nicotine Polacrilex 15% | | — | — |
| Nicotine Polacrilex 20% | | — | — |
| Nicotine Polacrilex 25% | | — | — |
| Magnesium stearate | 15.0 | 15.0 | 15.0 |
| Uncoated chewing gum mass | 1037.7 | 1347.9 | 1347.9 |
| | Example 29 (uncoated) | | |
| Composition of the chewing gum coating | | | |
| (a) mannitol; (b) xylitol; (c) sorbitol (provided as a 70% aqueous solution) | | (a) 69.0 (b) 391.0 | (a) 69.0 (c) 391.0 |
| Arabic gum | | 24.5 | 24.5 |
| Titanium dioxide | | 4.9 | 4.9 |
| Peppermint oil | | 7.5 | 7.5 |
| Levomenthol | | 4.3 | 4.3 |
| Talc | | q.s. (<0.1) | q.s. (<0.1) |
| Carnauba wax | | q.s. (<0.1) | q.s. (<0.1) |
| Coated chewing gum mass | | 1849.1 | 1849.1 |

Examples 32-34

Uncoated Nicotine Chewing Gums Comprising the Equivalent of 2 mg of Nicotine Base Each

| Composition of uncoated chewing gum | Example 32 | Example 33 | Example 34 |
| --- | --- | --- | --- |
| (Equivalent of Nicotine base included) | (2.0) | (2.0) | (2.0) |
| Compressible gum base (PG New Nutra TA, GumBase) | 1190.0 | — | — |
| Compressible gum base (Pharmagum, SPI) | — | 890.0 | — |
| Compressible gum base (All in Gum SF, Cafosa) | — | — | 890.0 |
| Aerosil ® | 5.0 | 5.0 | 5.0 |
| Acesulfame K | 1.5 | 1.5 | 1.5 |
| Orange flavor | 50.0 | 50.0 | 50.0 |
| Peppermint oil | 1.0 | — | — |
| Levomenthol | 8.0 | 10.0 | 10.0 |
| Coated sodium bicarbonate (Effersoda 12) | 50.0 | 50.0 | — |
| Sodium Carbonate | — | — | 10.0 |
| Sodium Bicarbonate | — | — | 20.0 |
| Mannitol | 10.0 | 10.0 | 10.0 |
| Talc | 10.0 | 10.0 | 10.0 |
| Nicotine bitartrate dihydrate | 6.4 | 6.4 | 6.4 |
| Nicotine Polacrilex 15% | — | — | — |
| Nicotine Polacrilex 20% | — | — | — |
| Nicotine Polacrilex 25% | — | — | — |
| Magnesium stearate | 15.0 | 15.0 | 15.0 |
| Uncoated chewing gum mass | 1346.9 | 1047.9 | 1027.9 |

Example 35

Coated Nicotine Chewing Gum Comprising the Equivalent of 4 mg of Nicotine Base

| | Example 35 |
| --- | --- |
| Composition of uncoated chewing gum | |
| (Equivalent of Nicotine base included) | (4.0) |
| Compressible gum base (All in Gum SF Cool, Cafosa) | 1190.0 |
| Aerosil ® | 5.0 |
| Acesulfame K | 1.5 |
| Mint flavor | 50.0 |
| Taste masking flavor | 20.0 |
| Levomenthol | 10.0 |
| Coated sodium bicarbonate (Effersoda 12) | 50.0 |
| Mannitol | 10.5 |
| Talc | 10.0 |
| Nicotine bitartrate dihydrate | 12.28 |
| Magnesium stearate | 15.0 |
| Uncoated chewing gum mass | 1496.3 |
| Composition of the chewing gum coating | |
| Maltitol (provided as 70% aqueous solution) | 451.2 |
| Maltitol powder | 66.7 |
| Arabic gum | 24.5 |
| Glycerol | 9.8 |
| Povidone K-30 | — |
| Copovidone VA 64 | — |
| Titanium dioxide | 4.9 |
| Peppermint oil | 7.5 |
| Levomenthol | 4.3 |
| Talc | q.s. (<0.1) |
| Carnauba wax | q.s. (<0.1) |
| Coated chewing gum mass | 2065.2 |

Test Example 1

The stability of the coated nicotine chewing gum of Example 14 was tested via an assay of nicotine. In doing so, the formulation was stored under various conditions (temperature/relative humidity) and for various storage times, and at the end the amount of nicotine still being present was determined (in %). The packaging used was a thermoformed blister made of tricomposite film of PVC/PE/PVdC (=polyvinyl chloride/polyethylene/polyvinylidene chloride) sealed with aluminium foil. The mean results obtained were as follows:

| Storage time/Condition | 25° C./60% r.h. | ambient | 30° C./75% r.h. |
| --- | --- | --- | --- |
| start | 100.8% | | |
| 1 month | 98.5% | n.t. | n.t. |
| 2 months | 99.9% | n.t. | n.t. |
| 6 months | 96.1% | n.t. | 98.0% |
| 12 months | 97.9% | 100.5% | 98.0% |

(n.t. = not tested)

It was demonstrated that the active substance is stable even under demanding storage conditions for long periods of time.

Test Example 2

The in-vitro release of nicotine from the chewing gums of the present invention was measured with the apparatus disclosed in Kvist et al., Int J Pharm 189 (1999) 57-65. As chewing machine, a device Erweka DRT 6 (from AB FIA, Lund, Sweden) was used. 40 ml of a buffer (pH 7.4) served as dissolution medium. The distance between the upper and lower chewing surfaces was 1.6 mm, the strokes frequency 50/min and the twist angle 20°. For the chewing gum of Example 14, the following mean in-vitro release of nicotine was observed (in % of total original nicotine content):

| Duration of chewing | | |
| --- | --- | --- |
| 5 min | 10 min | 30 min |
| 70.4% | 84.4% | 93.2% |

Test Example 3

The mean in-vivo truly delivered total doses delivered from the tested chewing gums (all containing the equivalent of 2 mg of nicotine free base) in the mouth of a patient over a time period of 30 minutes were measured (results see Table 1). Technically, this was done by determining the residual amount of nicotine in the chewed gums after 30 min of chewing.

TABLE 1

Truly delivered doses of nicotine (mg) - Comparative data

| | Nicorette ® 2 mg chewing gum | | 2 mg nicotine chewing gum of Example 14 | |
| --- | --- | --- | --- | --- |
| | Forced chew | Chew and park | Forced chew | Natural chew |
| Mean | 1.39 | 1.26 | 1.23 | 1.07 | 1.92 | 1.91 |
| Median | 1.42 | 1.25 | 1.28 | 1.04 | 1.92 | 1.91 |
| Min-Max | 1.13-1.59 | 0.69-1.69 | 0.52-1.53 | 0.54-1.60 | 1.83-1.98 | 1.81-1.98 |

The nicotine gum of the invention was found to deliver ca. 95% of its nominal amount whereas Nicorette® only delivered 50-60% thereof. Moreover, the inter-subject variability of the delivered dose was significantly lower in the nicotine gums of the present invention. This is beneficial because the desired higher nicotine plasma levels in the subjects willing to quit smoking will be reached faster and more reliably. This allows a faster craving relief and therefore a higher quitting rate.

Test Example 4

Nicotine Plasma Concentrations at Various Time Points and Corresponding AUCs—Comparative Data The plasma concentrations of nicotine reached after chewing the test nicotine gums in a well defined manner were measured (see Table 2) and AUCs at various time points derived from the corresponding pharmacokinetic curves (see Table 3).

TABLE 2

Ratios of mean nicotine plasma concentrations C observed with a chewing gum of the invention (Example 14) versus Nicorette ® at various time points

| | 2 mg nicotine chewing gum of Example 14 | | 2 mg nicotine chewing gum Nicorette ® |
| --- | --- | --- | --- |
| | Forced chew | Natural chew | Chew & park |
| C (5 min) | 3.26 (<.00014) | 3.48 (<.00009) | 1 |
| C (10 min) | 2.90 (<.0001) | 2.68 (<.0001) | 1 |
| C (20 min) | 1.76 (<.0001) | 1.60 (<.0001) | 1 |

The results from Table 2 show that significantly higher nicotine plasma concentrations were obtained within the first 10 minutes of chewing a gum of the invention, whatever the chewing rhythm, versus a standard nicotine chewing gum (Nicorette®).

The absolute mean values observed for Example 14 v. Nicorette® 2 mg were as follows.

C (5 min): 1.439 v. 0.130 ng/mL
C (10 min): 3.957 v. 1.317 ng/mL
C (20 min): 5.483 v. 3.696 mg/mL.

TABLE 3

Ratios of mean AUCs observed with a chewing gum of the invention (Example 14) versus Nicorette ® at various time points

| | 2 mg nicotine chewing gum of Example 14 | | 2 mg nicotine chewing gum Nicorette ® |
| --- | --- | --- | --- |
| | Forced chew | Natural chew | Chew & park |
| 0-5 min | 2.89 (0.0195) | 3.23 (0.0108) | 1 |
| 0-10 min | 4.21 (<.0001) | 4.25 (<.0001) | 1 |
| 0-20 min | 2.62 (<.0001) | 2.49 (<.0001) | 1 |

The results from Table 3 show that significantly higher nicotine AUCs (up to more than 4 times) were obtained within the first 10 minutes of chewing with a chewing gum of the invention, whatever the chewing rhythm, versus Nicorette®.

The absolute mean values observed for Example 14 v. Nicorette® 2 mg were as follows.

AUC (0-5 min): 0.036 v. 0.004 ng×h/mL
AUC (0-10 min): 0.264 v. 0.064 ng×h/mL
AUC (0-20 min): 1.060 v. 0.484 ng×h/mL.

Therefore, the results from Tables 2 and 3 show that the gums of the invention deliver nicotine significantly faster than Nicorette® over the first 10 minutes of chewing and therefore provide a faster craving relief within the first 10 minutes of craving with consequently a higher quitting rate.

The invention claimed is:

1. A stable chewing gum for use in nicotine replacement therapy comprising a coated core, the core comprising:
   a compressible chewing gum base that is suitable for tableting at ambient temperature,
   at least one nicotine active selected from the group consisting of pharmaceutically
   acceptable salts of nicotine and pharmaceutically acceptable, cellulose-free, nicotine
   complexes and resins,
   at least one buffering agent in homogeneous mixture with the nicotine active, said at least one buffering agent comprising particles comprising a core of sodium bicarbonate and an outer layer of sodium carbonate,
   whereby the core is tableted, and
   a coating free of nicotine active comprising 80-95% maltitol and 0.5-3% peppermint oil (based on total coating mass).

2. A chewing gum according to claim 1, wherein the at least one nicotine active is selected from the group consisting of pharmaceutically acceptable salts of nicotine.

3. A chewing gum according to claim 1, which is characterized by comprising the at least one nicotine active in an amount corresponding to from 0.2 to 8 mg of nicotine free base.

4. A chewing gum according to claim 1, wherein the coating comprises a binder selected from the group consisting of arabic gum, tragacanth gum, guar gum, acacia gum, xanthan gum, alginic acid, salts of alginic acid, gellan gum, glucomannan gum, carrageenan gum, karaya gum, locust bean gum, tara gum, gelatin and any mixtures thereof.

5. A chewing gum according to claim 1, wherein the coating comprises a coating-plastifying substance selected from the group consisting of glycerol, polyethylene glycol, propylene glycol, povidone (polyvinyl pyrrolidone), copovidone (vinyl pyrrolidone vinyl acetate copolymer), hydroxypropyl cellulose, hydroxypropyl methylcellulose, hydroxypropyl methylcellulose phthalate, diethyl phthalate, dibutyl phthalate, diacetin, triacetin, triethyl citrate, dibutyl citrate, acetyl tributyl citrate, acetyl triethyl citrate, 2 pyrrolidone and any mixtures thereof.

6. A chewing gum according to claim 1, wherein rapid nicotine release means releasing in an in-vitro dissolution testing method (40 ml buffer pH 7.4, chewing jaw distance 1.6 mm - 20° rotation, 50 chewing movements per minute) at least 60% in 5 minutes (250 chews), at least 70% in 10 minutes (500 chews) and more than 80% in 30 minutes (1500 chews) of the total nicotine content.

7. A chewing gum according to claim 1, wherein rapid nicotine release means in-vivo delivering to the mouth of a patient at least 80% of the original amount of nicotine originally being present in said chewing gum over a time period of 30 mm starting with administering said chewing gum.

8. A chewing gum according to claim 1, having a mean plasma concentration C (5 min) of from 1 up to 6 ng/ml.

9. A chewing gum according to claim 1, having a plasma concentration C (10 min) of from 3 up to 14 ng/ml.

10. A chewing gum according to claim 1, having a mean AUC (0-10 min) of from 0.2 up to 0.9 ng×h/ml.

11. A chewing gum according to claim 1, capable of reaching a mean AUC (0-20 min) of from 0.8 up to 3.2 ng×h/ml.

12. A chewing gum according to claim 1, wherein the coating additionally comprises a binder comprising a gum.

13. A chewing gum according to claim 12, wherein the coating additional comprises a coating-plastifying substance comprising glycerol.

14. A stable chewing gum for use in nicotine replacement therapy comprising a coated core, the core comprising:
   a compressible chewing gum base that is suitable for tableting at ambient temperature,
   at least one nicotine active selected from the group consisting of pharmaceutically
   acceptable salts of nicotine and pharmaceutically acceptable, cellulose-free, nicotine
   complexes and resins,
   at least one buffering agent in homogeneous mixture with the nicotine active, said at least one buffering agent comprising particles comprising a core of sodium bicarbonate and an outer layer of sodium carbonate,
   a binder selected from the group consisting of arabic gum, tragacanth gum, guar gum, acacia gum, xanthan gum, alginic acid, salts of alginic acid, gellan gum, glucomannan gum, carrageenan gum, karaya gum, locust bean gum, tara gum, gelatin and any mixtures thereof,
   whereby the core is tableted, and
   a coating free of nicotine active comprising 80-95% maltitol and 0.5-3% peppermint oil (based on total coating mass), and
   a coating-plastifying substance selected from the group consisting of glycerol, polyethylene glycol, propylene glycol, povidone (polyvinyl pyrrolidone), copovidone (vinyl pyrrolidone vinyl acetate copolymer), hydroxypropyl cellulose, hydroxypropyl methylcellulose, hydroxypropyl methylcellulose phthalate, diethyl phthalate, dibutyl phthalate, diacetin, triacetin, triethyl citrate, dibutyl citrate, acetyl tributyl citrate, acetyl triethyl citrate, 2 pyrrolidone and any mixtures thereof.

15. A chewing gum according to claim 14, wherein the coating-plastifying substance is glycerol.

16. A stable chewing gum for use in nicotine replacement therapy comprising a coated core, the core comprising
   a compressible chewing gum base suitable for tableting at ambient temperature, at least,
   one nicotine active selected from the group consisting of pharmaceutically acceptable,
   salts of nicotine and pharmaceutically acceptable, cellulose-free, nicotine complexes,
   and resins, and
   at least one buffering agent in homogeneous mixture with the nicotine active, said at least one buffering agent comprising particles comprising a core of sodium bicarbonate and an outer layer of sodium carbonate,
   whereby the core is tableted, and
   a coating which is optionally free of nicotine active.

17. A chewing gum according to claim 16, comprising the at least one nicotine active in an amount corresponding to from 0.2 to 8 mg of nicotine free base.

18. A chewing gum according to claim 17, comprising nicotine bitartrate as the nicotine active.

19. A chewing gum according to claim 16, wherein the coating comprises maltitol.

20. A chewing gum according to claim 19, wherein the coating comprises maltitol in an amount of 80-95% of the total coating mass and peppermint oil in an amount of 0.5-3% of the total coating mass.

21. A chewing gum according to claim 19, wherein the coating comprises a binder selected from the group consisting of arabic gum, tragacanth gum, guar gum, acacia gum, xanthan gum, alginic acid, salts of alginic acid, gellan gum, glucomannan gum, carrageenan gum, karaya gum, locust bean gum, tara gum, gelatin and any mixtures thereof.

22. A chewing gum according to claim 21, wherein the coating comprises a coating-plastifying substance selected from the group consisting of glycerol, polyethylene glycol, propylene glycol, povidone (polyvinyl pyrrolidone), copovidone (vinyl pyrrolidone vinyl acetate copolymer), hydroxypropyl cellulose, hydroxypropyl methylcellulose, hydroxypropyl methylcellulose phthalate, diethyl phthalate, dibutyl phthalate, diacetin, triacetin, triethyl citrate, dibutyl citrate, acetyl tributyl citrate, acetyl triethyl citrate, 2 pyrrolidone and any mixtures thereof.

23. A chewing gum according to claim 22 wherein the coating-plastifying substance comprises glycerol.

24. A chewing gum according to claim 16 having, wherein fast-but non-toxic, pharmaceutically acceptable - buccal absorption of nicotine means reaching a mean plasma concentration C (5 min) of from 1 up to 6 ng/ml.

25. A chewing gum according to claim 16, having a plasma concentration C(10 min) of from 3 up to 14 ng/ml.

26. A chewing gum according to claim 16, having a mean AUC (0-10 min) of from 0.2 up to 0.9 ng×h/ml.

27. A chewing gum according to claim 16, having a mean AUC (0-20 min) of from 0.8 up to 3.2 ng×h/ml.

28. A stable chewing gum for use in nicotine replacement therapy comprising a coated core, the core comprising:
a compressible chewing gum base suitable for tableting at ambient temperature, at least
one nicotine active selected from the group consisting of pharmaceutically acceptable salts of nicotine and pharmaceutically acceptable, cellulose-free, nicotine complexes and resins, and
at least one buffering agent in homogeneous mixture with the nicotine active, said at least one buffeting agent comprising particles comprising a core of sodium bicarbonate and an outer layer of sodium carbonate;
whereby the core is tableted, and the coating consisting essentially of;
a binder selected from the group consisting of arabic gum, tragacanth gum, guar gum, acacia gum, xanthan gum, alginic acid, salts of alginic acid, gellan gum, glucomannan gum, carrageenan gum, karaya gum, locust bean gum, tara gum, gelatin and any mixtures thereof, a coating-plastifying substance selected from the group consisting of glycerol, polyethylene glycol, propylene glycol, povidone (polyvinyl pyrrolidone), copovidone (vinyl pyrrolidone vinyl acetate copolymer), hydroxypropyl cellulose, hydroxypropyl methylcellulose, hydroxypropyl methylcellulose phthalate, diethyl phthalate, dibutyl phthalate, diacetin, triacetin, triethyl citrate, dibutyl citrate, acetyl tributyl citrate, acetyl triethyl citrate, 2 pyrrolidone and mixtures thereof, maltitol, peppermint oil, and optional flavors, colorants or antioxidants.

29. A chewing gum according to claim 28, wherein the nicotine active is nicotine bitartrate dihydrate.

30. A chewing gum according to claim 28, wherein the maltitol comprises 80-95% of the total coating mass.

31. A chewing gum according to claim 30, wherein the peppermint oil comprises 0.5-3% of the total coating mass.

* * * * *